US00PP08529P

United States Patent [19]

Nishida et al.

[11] Patent Number: Plant 8,529

[45] Date of Patent: Jan. 4, 1994

[54] JAPANESE PEAR TREE GOLD NIJISSEIKI

[75] Inventors: Teruo Nishida, Mito; Haruhiko Fujita, Matsumoto; Fukio Ikeda, Machida; Tetsuro Sanada; Kazuo Kotobuki, both of Tsukuba, all of Japan

[73] Assignee: National Institute of Agrobiological Resources, Ministry of Agriculture, Forestry and Fisheries, Tsukuba, Japan

[21] Appl. No.: 977,272

[22] Filed: Nov. 16, 1992

[51] Int. Cl.[5] ..... A01H 5/00

[52] U.S. Cl. ..... Plt./36

[58] Field of Search ..... Plt. 36

[56] References Cited

PUBLICATIONS

Sigurbjörnsson, 1983, *Crop Breeding*, pp. 153–176.

Kourik, 1990, *Country Life*, pp. 46–51.

*Primary Examiner*—James R. Feyrer

*Assistant Examiner*—Elizabeth C. Kemmerer

*Attorney, Agent, or Firm*—Armstrong, Westerman, Hattori, McLeland & Naughton

[57] ABSTRACT

The new and distinct cultivar relates to a Japanese pear tree that has a strong resistance to black spot disease and substantially has the same excellent qualities of "Nijisseiki" as a Japanese pear cultivar. This pear tree bears a yellowish green fruit, is moderately sweet and acidic, and has a good taste that is suitable for desserts.

10 Drawing Sheets

BACKGROUND OF THE CULTIVAR

The present invention relates to a new and distinct cultivar of Japanese pear tree (*Pyrus pyrifiolia*), and, particularly, to the tree bearing fruit with a yellowish-green skin, having characteristics substantially the same as those of "Nijisseiki", but having a significantly strong resistance to black spot disease.

In Japan, "Nijisseiki", which is considered a chance seedling, is an excellent cultivar that is gradually increasing in popularity so as to comprise about 40 percent of the total cultivation area of the Japanese pear tree to date. It has, however, a severe shortcoming in that "Nijisseiki" has a high susceptibility to black spot disease, and thus it is only capable of being cultivated on a large scale in an area having little rain from spring through summer.

The black spot disease is developed on the leaf, stem and the fruit of "Nijisseiki" tree, in particular, the young fruit is associated with the formation of black and rounded lesions, and cracking.

One objective of the present inventors is to provide an improved cultivar of the pear fruit tree having a strong resistance to black spot disease, while also having the excellent characteristics of the "Nijisseiki".

ORIGIN AND ASEXUAL REPRODUCTION OF THE CULTIVAR

The new cultivar of Japanese pear tree was derived from "Nijisseiki" by mutation breeding. In 1962, nursery stocks of "Nijisseiki" were planted at a gamma field of the Institute of Radiation Breeding National Institute of Agrobiological Resources, Ministry of Agriculture, Forestry and Fisheries, Omiya-machi, Naka-gun, Ibaraki, Japan, and have been continuously exposed to γ-rays hitherto. In 1981, the amount of fungicide sprayed on the trees was reduced and one of the trees developed a branch devoid of the symptoms associated with black spot disease. It has been confirmed that the said bough has a significantly strong resistance to black spot disease compared to "Nijisseiki". The branch was top-grafted on rootstocks to subject same to a local adaptability test at the fields of each prefectural experimental station located in Tottori, which is the main production region of "Nijisseiki", Nagano, Fukushima, and the like, since 1986.

As a result, the trees bore fruit for the first time in 1988, and it was found that the trees have a significantly strong resistance to black spot disease compared to "Nijisseiki" while also displaying the excellent characteristics of the Nijisseiki. For instance, in 1989, the trees had not developed lesions of black spot disease on the leaves, stem or fruit based upon the susceptibility to black spot disease field tests. In the past in trees that had black spot disease, 90 percent of the total leaves of "Nijisseiki" were damaged, but the value for this new cultivar tree was only 5 percent at the Nagano-ken Nanshin Agricultural Experimental Station, and 6.9 percent at the Gunma-ken Horticultural Experimental Station.

The present inventors named the new tree "Gold Nijisseiki".

This new and distinct cultivar of Japanese pear tree "Gold Nijisseiki" was asexually reproduced by grafting, at the various Prefectural Experimental Stations, and confirmed the homogeneity and stability thereof.

An application for this new cultivar of Japanese pear tree "Gold Nijisseiki" under the Seeds and Seedlings Law of Japan was filed on Mar. 26, 1990, and registered under Number 2932 on Dec. 16, 1991.

In the following description, the color-coding is in accordance with the Inter-Society Color Council-National Bureu of Standards (ISCC-NBS Color Name).

The new cultivar of Japanese pear tree according to the present invention was developed inadvertently from "Nijisseiki" by mutation breeding using γ-rays as a mutagen. As described above, "Nijisseiki" which is the parent cultivar, was obtained as a chance seedling before 1900, and was widely cultivated in Japan. The main characteristics of the parent cultivar are as follows:

Tree:

*Vigor.*—Habit of branches is medium. The unpruned tree may have a height of about 7 m and a width of about 4 m when 15 years old. When the tree was grafted on a root stock, which is a seedling stock of Japanese pear, and cultivated for 10 years, a vegetative shoot of the tree extended to 70–80 cm per year.

*Spur.*—Easy to maintain. The number of spurs is 12 per meter of branch.

*Predominance of axillary flower bud.*—Few(5.8%).

*Time of bud break.*—Medium, around April 9th, at Ibaraki prefecture, Japan.

*Production.*—High productivity.

*Cross-compatibility.*—Cross-compatible with, e.g., "Chojuro", "Kosui". The tree is self-incompatible and is manually pollinated. The fruit set percentage is 90–100%.

*Bark.*—The bark texture of the new and old wood is hard, and the bark of a 10 year old tree may be cracked. The lenticels of the new and old wood are medium, and density thereof is medium (110/10 cm).

Branches (shoot):

*Length.*—Medium, about 78.8 cm at one year old.

*Thickness.*—Stout, about 8.78 mm.

*Length of internode.*—Short, about 4.3 cm.

*Color.*—Light green brown (ISCC-NBS, Strong Yellowish Brown).

*Density of pubescence.*—High.

*Angle between leaf bud and shoot.*—Medium, about 26.8°.

Leaves:

*Shape.*—Oval.

*Size.*—Medium (11.1 cm×6.7 cm).

*Color.*—Dark Green (ISCC-NBS, Dark Green).

*Length of petiole.*—Short, about 2.6 cm.

*Thickness of petiole.*—Medium, about 2.4 mm.

*Color of young leaves.*—Brown (ISCC-NBS, Deep Reddish Brown).

*Density of pubescence of young leaves.*—High.

Flowers:

*Flower number in a flower cluster.*—Slightly more than medium, about 10.25 on average.

*Size.*—Medium, about 3.4 cm.

*Color.*—Light pink (ISCC-NBS, Light Pink) calyx, coloration at blooming fades to pure white (ISCC-NBS, Whilte) with flower opening.

*Shape of petals.*—Round.

*Notch of margin of petals.*—Medium.

*Number of petals.*—Slightly more than medium, 5.56 pieces on average.

*Color of anther.*—Strong red (ISCC-NBS, Strong Red).

*Number of stamens.*—Slightly more than medium, 27.1 on average.

*Number of pollen.*—Much.

*Flowering time.*—Middle in the season.

*Flowering data and full bloom stage.*—April 20th and April 24th at the Institute of Radiation Breeding, NIAR, on average from 1987 to 1989.

Fruit:

*Size.*—323 g on average.

*Shape.*—Round.

*Color of skin (unbagged fruit).*—Yellowish green (ISCC-NBS, Light Yellow Green).

*Calyx perpetual fruit.*—Absent.

*Size of dot.*—Medium.

*Density of dot.*—Medium.

*Color of flesh.*—Yellowish white (ISCC-NBS, Pale Greenish Yellow).

*Flesh.*—Soft and juicy. The firmness is about 4.26 lbs. according to Magness-Teller's hardness meter index. The fruit can be stored at 20°–25° C. for 15 days.

*Length of peduncle.*—Medium, 3.6 cm on average.

*Thickness of peduncle.*—Stout, 4.3 mm on average.

*Color of peduncle.*—Dull green (ISCC-NBS, Moderate Yellowish Green)

*Color of dot.*—Dull Yellow (ISCC-NBS, Moderate Yellow).

*Color of core.*—Yellowish White (ISCC-NBS, Yellowish White).

*Shape of core.*—Short conical.

*Size of core.*—Medium (core/fruit=40/87, at transverse diameter).

*Seed cells.*—5 cells per fruit, about 1.7 seeds per cell, 4–5 seeds per well shaped fruit.

*Size of seeds.*—Medium, 8.9 mm×5.9 mm on average.

*Shape of seeds.*—Oval.

*Taste.*—Moderate sweetness, the sugar content of the fruit juice is about 10.9%, a medium acidity, pH 4.8, and no astringency. Although the taste of the fruit at skin/flesh interface cannot be distinguished, the taste of the core flesh tissues surrounding the seed cells has slightly higher acidity than other parts.

*Bagged.*—The bagged fruit has a slightly fine appearance compared to fruit that has not been bagged, but the latter is less than the former in sweetness. Color of both are not distinguishable from each other, but in the unbagged fruit, cork spots are slightly more apparent than in the bagged fruit.

*Maturity.*—Ripening middle in the season, e.g., September 16–25th at the Institute of Radiation Breeding, NIAR.

*Use.*—Suitable for dessert.

*Keeping quality.*—Can be kept for about 15 days at 20°–25° C.

Resistance to diseases: Has a high susceptibility to black spot disease and susceptibility to pear necrotic spot virus, but has minor susceptibility to pear scab. The tree is not susceptible to pear canker.

Cold resistant: Almost the same as that of other Japanese pears.

Core breakdown: Absent.

Watercore; Slightly apparent.

Fruit cracking: None.

Culture: The shape and uniformity of the fruit shows a tendency to disperse, but these problems can be solved by usual fruit thinning methods.

The cultivar "Nijisseiki" is widely cultivated, and its seedling is easily available in Japan.

SUMMARY OF THE INVENTION

This new cultivar of Japanese pear tree "Gold Nijisseiki" has a strong vigor, a strong trunk and a short internode, a high productivity and a high quality fruit, and thus the characteristics of the tree are substantially the same as those of "Nijisseiki", except that the present "Gold Nijisseiki" has a significantly strong resistance to black spot disease, and flowering time, is a few days earlier than "Nijisseiki". The present tree has an affinity to "Chojuro", "Kosui" etc. in connection with pollination. The tree has a width of about 7 meters and height of about 2.5 meters when the tree is treated with trellis training to a height of about 1.8 meters. The tree has medium branching habits and medium branch density when unpruned. When the tree is conventionally treated with trellis training and pruned, vegetative shoots and succulent spouts grow well, and further, the tree canopy develops quickly. When a ten year old tree was cultivated in the central part of the Kanto district, e.g., Ibaraki prefecture, Japan, a vegetative shoot was extended by 70–80 cm, on average. The crotch angles formed by branches are about 47 degrees. The tree produces a round-shaped fruit that matures in the middle of the season, e.g., from the middle to the end of September, in the central part of Kanto distinct, Japan.

The fruit has a medium size, i.e., 300–350 g, a yellowish-green skin, and yellowish-white flesh that is soft and a moderate texture. The fruit juice has a moderate Brix, and moderate acidity at a pH of about 4.47.

DESCRIPTION OF THE CULTIVAR

Figure 1:
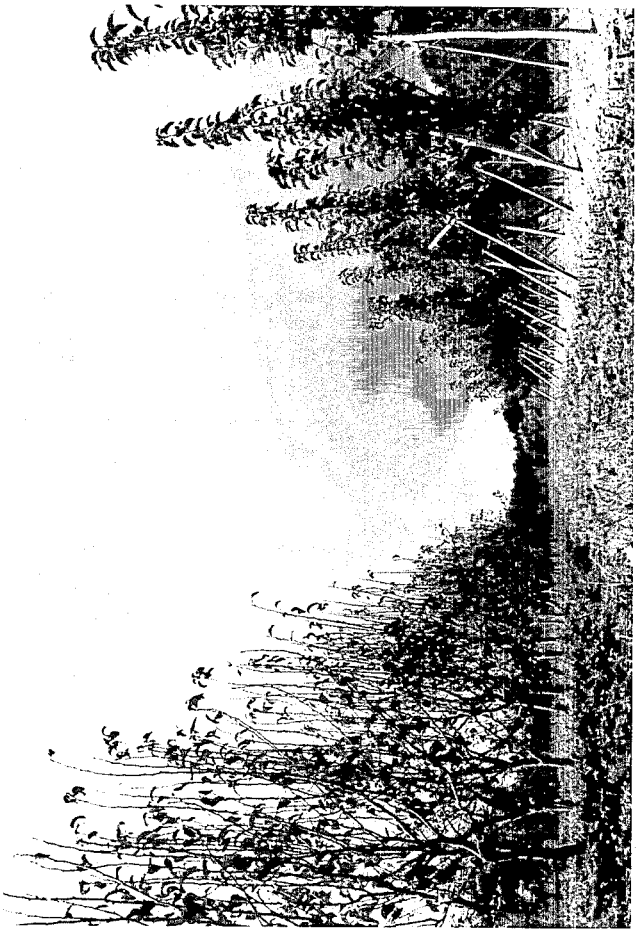
FIG. 1 is a photograph of a shape of the new cultivar of Japanese pear tree "Gold Nijisseiki"
Figure 2:
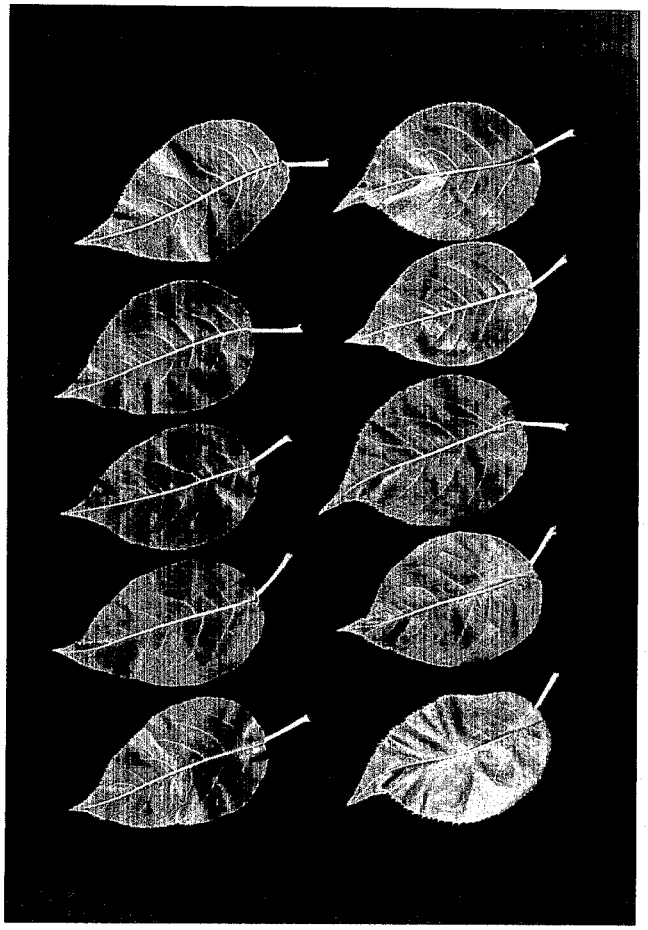
FIG. 2 is a photograph of adult leaves, the upper row being adaxial of the new cultivar of Japanese pear tree.
Figure 3:
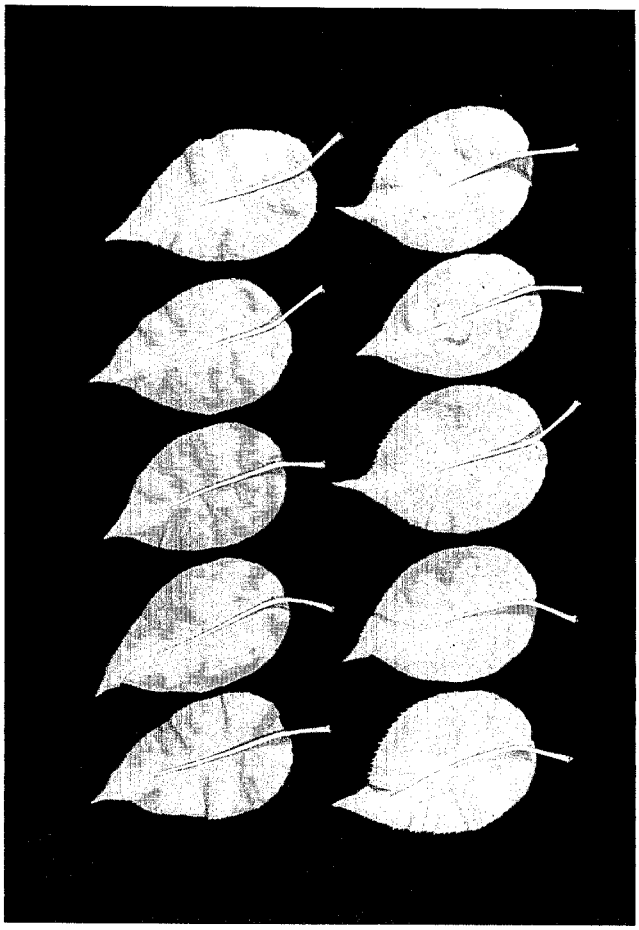
FIG. 3 is a photograph of adult leaves, the lower one being abaxial of the new cultivar of Japanese pear tree.
Figure 4:
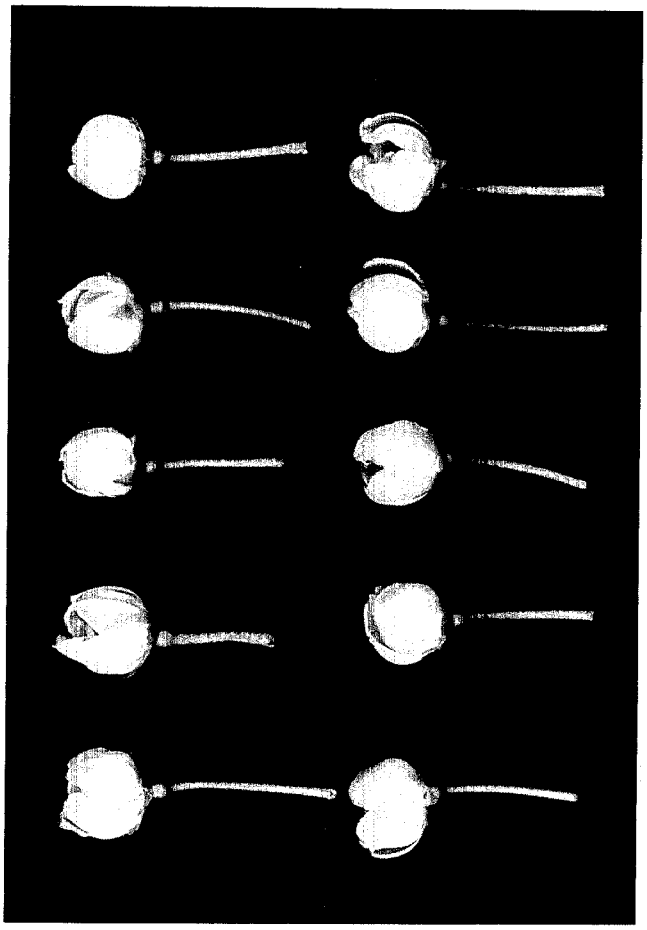
FIG. 4 is a photograph of the flower in the bud stage of the new cultivar of Japanese pear.
Figure 5:
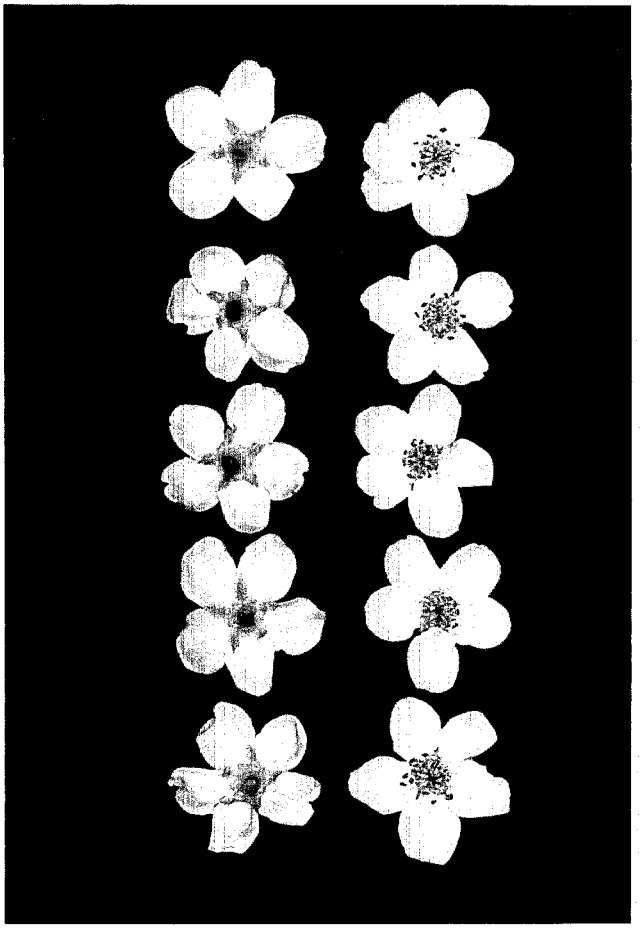
FIG. 5 is a photograph of the flower of the new cultivar of Japanese pear tree.
Figure 6:
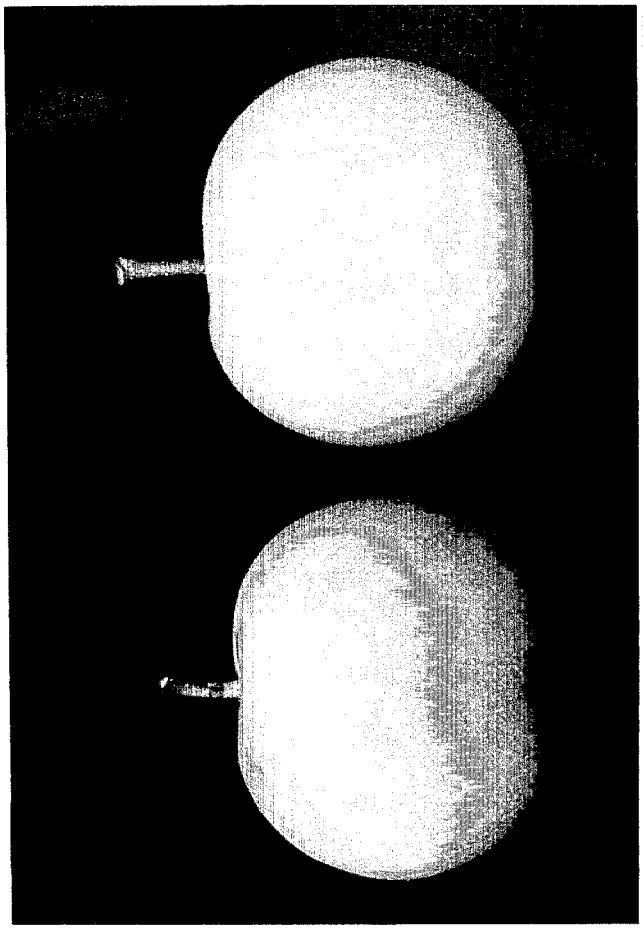
FIG. 6 is a photograph of the side of fruit of the new cultivar of Japanese pear tree.
Figure 7:
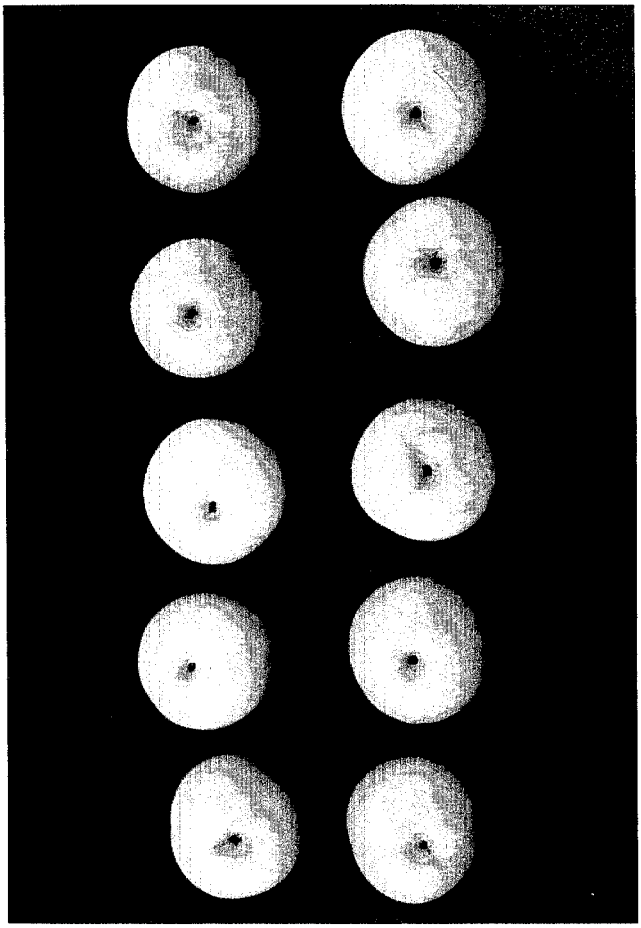
FIG. 7 is a photograph of views at the blossom end of fruit of the new cultivar of Japanese pear tree.
Figure 8:
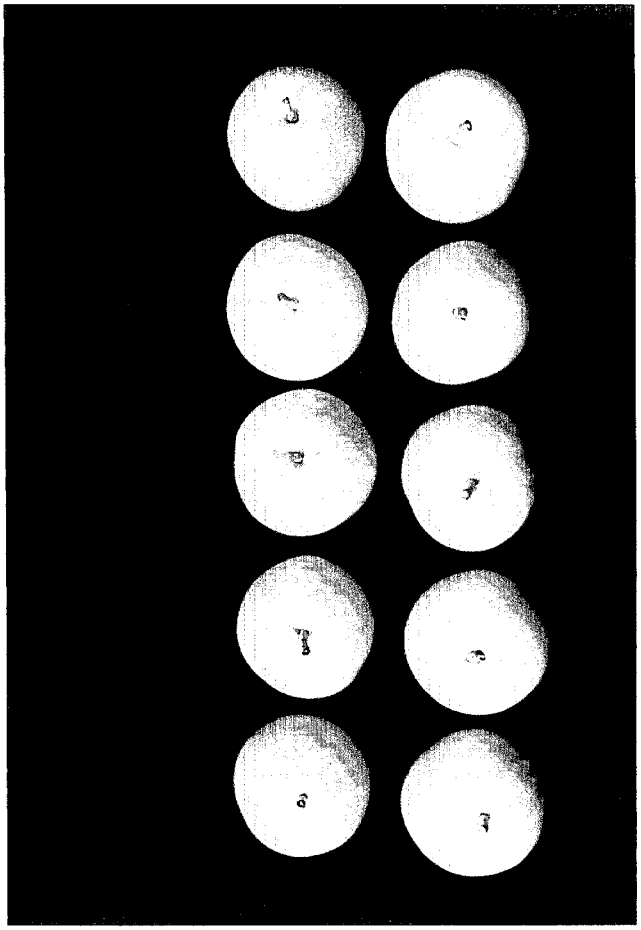
FIG. 8 is a photograph of views at the stem end of fruit of the new cultivar of Japanese pear tree.
Figure 9:
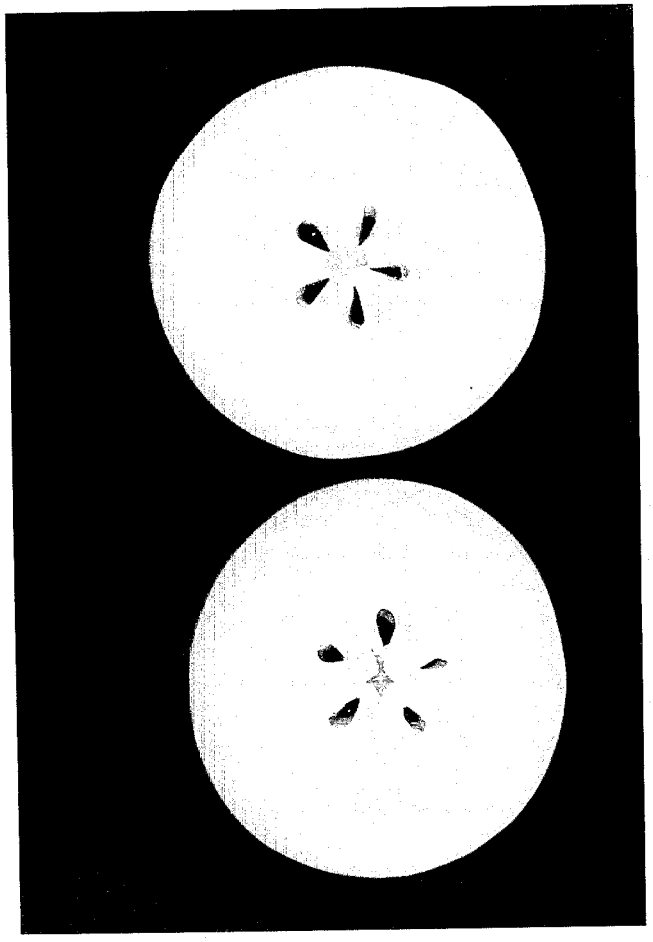
FIG. 9 is a photograph of cross-sectional view of fruit of the new cultivar of Japanese pear tree.
Figure 10:
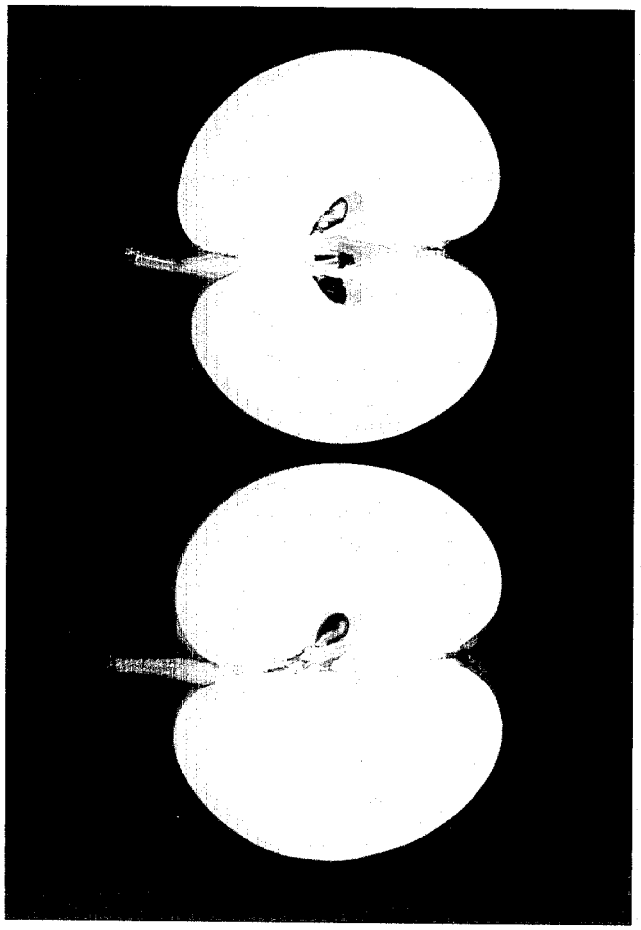
FIG. 10 is a photograph of longitudinal-sectional view of fruit of the new cultivar of Japanese pear tree.

The characteristics of the new and distinct cultivar of Japanese pear tree "Gold Nijisseiki" are as follows:

Tree:

*Vigor.*—Habit of branches is medium. The unpruned tree may have a height of about 7 m and a width of about 4 m when 15 years old. When the tree was grafted on a root stock, which is a seedling stock of Japanese pear, and cultivated for 10 years, a vegetative shoot of the tree extended to 70–80 cm per year.

*Spur.*—Easy to maintain. The number of spurs is 12 per meter of branch.

*Predominance of axillary flower bud.*—Few (7.4%).

*Time of bud break.*—Middle, around April 7th, at the Institute of Radiation Breeding, NIAR, Japan.

*Production.*—High productivity.

*Cross-compatibility.*—Cross-compatible with, e.g., "Chojuro", "Kosui". The tree is self-incompatible and is manually pollinated. The fruit set percentage is 90–100%.

*Bark.*—The bark texture of the new and old wood is hard, and the bark of a 10 year old tree may be cracked. The lenticels of the new and old wood are medium, and density thereof is medium (122 lenticels/10 cm).

Branches (shoot):

*Length.*—Medium, about 73.1 cm at one year old.

*Thickess.*—Stout, about 9.05 mm.

*Length of internode.*—Short, about 4.3 cm.

*Color.*—Light green brown (ISCC-NBS, Strong Yellowish Brown).

*Density of pubescence.*—High.

*Angle between leaf bud and shoot.*—Medium, about 26.0°.

Leaves:

*Shape.*—Oval.

*Size.*—Medium (11.2 cm×6.9 cm).

*Color.*—Dark Green (ISCC-NBS, Dark Green).

*Length of petiole.*—Short, about 2.5 cm.

*Thickness of petiole.*—Medium, about 2.4 mm.

*Color of young leaves.*—Brown (ISCC-NBS, Deep Reddish Brown).

*Density of pubescence of young leaves.*—High.

Flowers:

*Flower number in a flower cluster.*—Slightly more than medium, about 9.65 on average.

*Size.*—Medium, about 3.4 cm.

*Color.*—Light pink (ISCC-NBS, Light Pink) calyx, coloration at blooming fades to pure white (ISCC-NBS, White) with flower opening.

*Shape of petals.*—Round.

*Notch of margin of petals.*—Medium.

*Number of petals.*—Slightly more than medium, 5.54 pieces on average.

*Color of anther.*—Strong red (ISCC-NBS, Strong Red).

*Number of stamens.*—Slightly more than medium, 26.2 on average.

*Number of pollen.*—Much.

*Flowering time.*—Middle in the season.

*Flowering date and full bloom stage.*—April 19th and April 22th at the Institute of Radiation Breeding, NIAR, on average from 1987 to 1989.

Fruit:

*Size.*—325 g on average.

*Shape.*—Round.

*Color of skin (unbagged fruit).*—Yellowish green (NSCC-NBS, Light Yellow Green).

*Calyx perpetual fruit.*—Absent.

*Size of dot.*—Medium.

*Density of dot.*—Medium.

*Color of flesh.*—Yellowish white (ISCC-NBS, Pale Greenish Yellow).

*Flesh.*—Soft and juicy. The firmness is about 4.03 lbs. according to Magness-Teller's hardness meter index. The fruit can be stored at 20°–25° C. for 15 days.

*Length of peduncle.*—Medium, 3.1 cm on average.

*Thickness of peduncle.*—Stout, 3.8 mm on average.

*Color of peduncle.*—Dull green (ISCC-NBS, Moderate Yellowish Green).

*Color of dot.*—Dull green (ISCC-NBS, Moderate Yellow).

*Color of core.*—Yellowish white (ISCC-NBS, Yellowish White).

*Shape of core.*—Short conical.

*Size of core.*—Medium (core/fruit=38/89, at transverse diameter).

*Seed cells.*—5 cells per fruit, about 1.7 seeds per cell, 4–5 seeds per well shaped fruit.

*Size of seeds.*—Medium, 9.0 mm×5.7 mm on average.

*Shape of seeds.*—Oval.

*Taste.*—Moderate sweetness, the sugar content of the fruit juice is about 10.3%, a medium acidity, pH 4.47, and no astringency. Although the taste of the fruit at skin/fresh interface cannot be distinguished, the taste of the core flesh tissues surrounding the seed cells has slightly higher acidity than other parts.

*Bagged.*—The bagged fruit has a slightly fine appearance compared to fruit that has not been bagged, but the latter is less than the former in sweetness. Color of both are not distinguishable from each other, but in the unbagged fruit cork spots are slightly more apparent than in the bagged fruit.

*Maturity.*—Ripening middle in the season, e.g., September 16–25th at the Institute of Radiation Breeding, NIAR.

*Use.*—Suitable for dessert.

*Keeping quality.*—Can be kept for about 15 days at 20°–25° C.

Resistance to diseases: In a test using a spore of *Alternaria kikuchiana,* which is pathogenic fungi that induces Black spot disease, in the laboratory, a resistant cultivar "Chojuro" developed symptoms for about 20% of the second leaves, thereafter the symptoms decreasing or disappearing as leaf age increases, while "Nijisseiki" was 100% diseased in the second through fifth leaves. When inoculated with the spores, the present tree "Gold Nijisseiki" developed symptoms for about 80% and about 17% of the second and third leaves, respectively, but the fourth or greater leaves displayed no symptoms. As a result, it is confirmed that although the present tree "Gold Nijisseiki" has a slightly lower resistance to black spot disease than the tree "Chyojuro", the present tree has a significantly higher resistance to black spot disease than the parent tree "Nijisseiki". In field cultivation, the present trees did not develop the similar symptoms when subjected to the same control methods for black spot disease as those applied to the resistant cultivar, and if there were symptoms, the lesion of the leaves did not extend, and only the lesion part, which was dried and grayish brown in color, was deleted from the leaf. Thus, the present tree did not suffer from leaf abscission as much as "Nijisseiki". Furthermore, 60% of the young fruit of "Nijisseiki" experienced cracking. In contrast, there was scarcely no disease or injury on the present tree. The present tree has susceptibility to pear necrotic spot virus, and has minor susceptibility to pear scab. The tree is not susceptible to pear canker.

Cold resistant: Almost the same as that of other Japanese pears.

Core breakdown: Absent.

Watercore: Slightly observed.

Fruit cracking: None.

Culture: The shape and uniformity of the fruit shows a tendency to disperse, but these problems can be solved by usual fruit thinning methods.

The new cultivar of Japanese pear tree "Gold Nijisseiki" is cultivated and kept at the Institute of Radiation Breeding, National Institute of Agrobiological Resources, Omiya-machi, Naka-gun, Ibaraki, Japan.

Since the new cultivar, "Gold Nijisseiki", has a strong resistance to black spot disease, and has excellent dessert quality, etc., the trees of the present cultivar can be conveniently and easily cultivated in various agricultural districts.

We claim:

1. A new and distinct cultivar of Japanese pear tree bearing a yellowish green fruit, substantially as herein illustrated and described, characterized by its vigorous, medium growth and its ability to produce a medium size fruit having soft, yellowish white flesh that flowers about 2 days earlier than "Nijisseiki", and has a significantly strong resistance to black spot disease compared to "Nijisseiki"; the fruit is further characterized by its good taste which is moderately sweet and acidic, and its keeping quality.

* * * * *